(12) United States Patent
Carrier (10) Patent No.: US 11,490,886 B2
(45) Date of Patent: Nov. 8, 2022

(54) BONE FIXATION SYSTEM (71) Applicant: THE BRIGHAM AND WOMEN'S HOSPITAL, INC., Boston, MA (US)

(72) Inventor: Charles S. Carrier, Newton, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 92 days.

(21) Appl. No.: 17/057,219

(22) PCT Filed: May 22, 2019

(86) PCT No.: PCT/US2019/033564
§ 371 (c)(1),
(2) Date: Nov. 20, 2020

(87) PCT Pub. No.: WO2019/226796
PCT Pub. Date: Nov. 28, 2019

(65) Prior Publication Data
US 2021/0212739 A1  Jul. 15, 2021

Related U.S. Application Data

(60) Provisional application No. 62/674,975, filed on May 22, 2018.

(51) Int. Cl.
*A61B 17/86* (2006.01)
*A61B 17/68* (2006.01)
(Continued)

(52) U.S. Cl.
CPC ........ *A61B 17/0401* (2013.01); *A61B 17/683* (2013.01); *A61B 17/864* (2013.01); *A61B 17/8685* (2013.01); *A61B 17/8869* (2013.01)

(58) Field of Classification Search
CPC .......................... A61B 17/0401; A61B 17/864
See application file for complete search history.

(56) References Cited

U.S. PATENT DOCUMENTS 6,293,961 B2   9/2001   Schwartz et al.
6,641,617 B1   11/2003  Merrill et al.
(Continued)

FOREIGN PATENT DOCUMENTS

WO   2017035186 A1   3/2017

OTHER PUBLICATIONS

Zimmer Herbert Cannulated Bone Screw; [https://www.zimmerbiomet.lat/content/dam/zimmer-biomet/medical-professionals/000-surgical-techniques/trauma/zimmer-herbert-cannulated-bone-screw.pdf]; 97-1155-401-00 Rev. 3 Jul. 27, 2015 © 2015 Zimmer, Inc.; retrieved on Jan. 25, 2022 (4 pages).
(Continued)

*Primary Examiner* — Christian A Sevilla
(74) *Attorney, Agent, or Firm* — Quarles & Brady LLP (57) ABSTRACT

A bone fixation system includes a length of suture, a screw, a tensioning tab, and an anchor. The length of suture has a first end and a second end. The screw comprises an elongated shaft having a threaded external surface, wherein the screw has a distal end, a proximal end, and an internal surface defining a passageway within the screw extending between the distal end and the proximal end, wherein the passageway is configured to receive the length of suture. The tensioning tab is affixed to a section of the length of suture. The anchor is configured to secure the first end of the length of suture adjacent to the proximal end of the screw.

16 Claims, 10 Drawing Sheets

(51) Int. Cl.
*A61B 17/88* (2006.01)
*A61B 17/04* (2006.01)

(56) References Cited

U.S. PATENT DOCUMENTS

| | | | |
|---|---|---|---|
| 8,911,502 B2 | 12/2014 | Li et al. | |
| 8,961,576 B2* | 2/2015 | Hodge | A61B 17/0401 |
| | | | 606/328 |
| 9,707,085 B2 | 7/2017 | Muratoglu et al. | |
| 2002/0120270 A1* | 8/2002 | Trieu | A61F 2/446 |
| | | | 606/279 |
| 2007/0203498 A1* | 8/2007 | Gerber | A61B 17/0401 |
| | | | 606/328 |
| 2010/0198258 A1* | 8/2010 | Heaven | A61B 17/0401 |
| | | | 606/232 |
| 2013/0190817 A1* | 7/2013 | Bouduban | A61B 17/864 |
| | | | 606/232 |
| 2014/0155944 A1 | 6/2014 | Truman | |
| 2014/0194907 A1 | 7/2014 | Bonutti et al. | |
| 2016/0206358 A1 | 7/2016 | Zhao et al. | |
| 2016/0345955 A1 | 12/2016 | Lizardi | |
| 2017/0135820 A1 | 5/2017 | Muratoglu et al. | |
| 2017/0156772 A1 | 6/2017 | Brinker et al. | |

OTHER PUBLICATIONS

International Search Report and Written Opinion dated Aug. 16, 2019 for International Application No. PCT/US2019/033564.

* cited by examiner

BONE FIXATION SYSTEM

CROSS-REFERENCES TO RELATED APPLICATIONS

This application is a 371 application of PCT/US19/33564 filed May 22, 2019 which is based on and claims priority to U.S. Provisional Patent Application No. 62/674,975, filed on May 22, 2018, and entitled "CannuCord: Cannulated Screw-Tension Cord Construct," the entire disclosure of PCT/US19/33564 and U.S. 62/674,975 being incorporated herein by reference.

STATEMENT REGARDING FEDERALLY SPONSORED RESEARCH

Not Applicable.

BACKGROUND OF THE INVENTION

The invention relates to orthopedic hardware for the purpose of bone fixation.

In practice, methods of bone and fracture fixation have long been dominated by plate and screw constructs. Plate and screw constructs provide rotational and vertical control to a fracture site, including a single bone or at a joint. Unfortunately, in use, screws tend to exhibit loosening and weakness when challenged by external forces.

Additional methods of fixation in practice include the use of suture systems. Sutures often must be passed through bone tunnels to repair soft tissue or bone. In this technique, sutures are passed through bone tunnels and tied over a post or button on the opposite side. In suture systems, the strength depends on cortical opposition to a grapple-like hook, as opposed to the rotation friction obtained via screw threads. While axial pullout strength of suture systems have proven to be greater than traditional plate and screw constructs, the rotational control and control against forces acting in a direction other than the suture axis have proven to be inferior to that provided by screws.

Therefore, there is a need for an improved bone fixation system that is capable of providing rotational control and axial strength perpendicular to the fixation site.

SUMMARY OF THE INVENTION

The foregoing needs are met by a bone fixation system according to the present disclosure.

In one aspect, the present disclosure provides a bone fixation system comprising a length of suture, a screw, a tensioning tab, and an anchor. The length of suture has a first end and a second end. The screw comprises an elongated shaft having a threaded external surface, wherein the screw has a distal end, a proximal end, and an internal surface defining a passageway within the screw extending between the distal end and the proximal end. The passageway can be configured to receive the length of suture. The tensioning tab is affixed to a section of the length of suture, wherein the section may be a midsection between the first end and the second end of the length of suture. The anchor is configured to secure the first end of the length of suture adjacent to the proximal end of the screw.

The anchor may further be configured to secure the second end of the length of suture adjacent to the proximal end of the screw and can be dimensioned to create an interference fit inside the passageway of the screw. The internal surface of the screw may include a threaded portion at the proximal end of the screw configured to engage the anchor. The anchor may further include external threads configured to engage the threaded portion of the internal surface of the screw. The anchor may further include at least one through hole configured to receive the length of suture. The suture may comprise a knot configured to engage the anchor. The bone fixation system may further comprise a button configured to engage the anchor and the length of suture. The distal end of the screw may terminate in a smooth tip.

The tensioning tab may further be dimensioned to navigate from a first side of a bone tunnel to a second side of the bone tunnel, wherein the bone tunnel extends from a first bone surface to a second bone surface, and the tensioning tab can be configured to engage the second bone surface. The tensioning tab may further include a first and second aperture. The elongated shaft of the screw may extend through the bone tunnel from the first bone surface to substantially adjacent to the second bone surface. The bone tunnel may extend through, but is not limited to, a tibia, a fibula, a femur, an acetabulum, a vertebra, and/or and an ankle joint comprised of the tibia and fibula.

In another aspect, the present disclosure provides a method for performing bone fixation. The method includes the steps of: (a) creating a bone tunnel extending from a first outer surface of a bone to a second outer surface of the bone; (b) moving an externally threaded cannulated screw and a length of suture through the bone tunnel until a proximal end of the screw is adjacent to the first outer surface and a distal end of the screw is substantially adjacent to the second outer surface; (c) engaging a tensioning tab at the second outer surface; (d) affixing the tensioning tab to a section of the length of suture; and (e) securing a first end of the length of suture adjacent to the proximal end of the cannulated screw using an anchor.

The section of the length of suture may be a midsection between the first end and the second end of the length of suture. The anchor may further be configured to secure the second end of the length of suture adjacent to the proximal end of the screw and dimensioned to create an interference fit inside the proximal end of the screw. Alternatively or additionally, the anchor may include external threads configured to engage a threaded portion of an internal surface of the screw, located at the proximal end. The anchor may further include at least one through hole configured to receive the length of suture. The length of suture may further include a knot configured to engage the anchor. Additionally or alternatively, a button may be configured to engage the anchor and the length of suture. The distal end of the screw may terminate in a smooth tip.

The tensioning tab may further be dimensioned to navigate from a first side of a bone tunnel to a second side of the bone tunnel, wherein the bone tunnel extends from a first bone surface to a second bone surface, and the tensioning tab is configured to engage the second bone surface. The tensioning tab may further include a first and second aperture. The elongated shaft of the screw may extend through the bone tunnel from the first bone surface to substantially adjacent to the second bone surface. The bone tunnel may extend through, but is not limited to, a tibia, a fibula, a femur, an acetabulum, a vertebra, and/or and an ankle joint comprised of the tibia and fibula.

In another aspect, the present disclosure provides a method for performing bone fixation. The method includes the steps of: (a) creating a bone tunnel extending from a first outer surface of a first bone to a second outer surface of a second bone; (b) moving an externally threaded cannulated screw and a length of suture through the bone tunnel until a proximal end of the screw is adjacent to the first outer surface and a distal end of the screw is substantially adjacent to the second outer surface; (c) engaging a tensioning tab at the second outer surface; (d) affixing the tensioning tab to a section of the length of suture; and (e) securing a first end of the length of suture adjacent to the proximal end of the cannulated screw using an anchor.

The section of the length of suture may be a midsection between the first end and the second end of the length of suture. The anchor may be further configured to secure the second end of the length of suture adjacent to the proximal end of the screw and dimensioned to create an interference fit inside the proximal end of the screw. Alternatively or additionally, the anchor may include external threads configured to engage a threaded portion of an internal surface of the screw, located at the proximal end. The anchor may further include at least one through hole configured to receive the length of suture. The length of suture may further include a knot configured to engage the anchor. Additionally or alternatively, a button may be configured to engage the anchor and the length of suture. The distal end of the screw may terminate in a smooth tip.

The tensioning tab may further be dimensioned to navigate from a first side of a bone tunnel to a second side of the bone tunnel, wherein the bone tunnel extends from a first bone surface to a second bone surface, and the tensioning tab is configured to engage the second bone surface. The tensioning tab may further include a first and second aperture. The elongated shaft of the screw may extend through the bone tunnel from the first bone surface to substantially adjacent to the second bone surface. The bone tunnel may extend through, but is not limited to, a tibia, a fibula, a femur, an acetabulum, a vertebra, and/or and an ankle joint comprised of the tibia and fibula.

A bone fixation system according to the present disclosure achieves a low profile solution that utilizes the rotational control of screws with the pullout strength of suture buttons/tension cords, using a cannulated screw that interfaces directly with a tension cord system. The screw can be placed and the tension cord (e.g., suture) can be deployed directly through the screw, protecting against in-line pullout. The bone fixation system can be used for environments including (without limitation): (1) ankle syndesmotic fixation; (2) total hip arthroplasty acetabular fixation; (3) vertebral body pedicle screw fixation; (4) tibial plateau fixation; and (5) femoral head fracture fixation.

The screw of a bone fixation system according to the present disclosure can act as in-line counter-traction in order to assist the tensioning suture to pull two structures together. The bone fixation system may include a round tipped screw and/or the beginning of the cannulated portion may have an inner screw device to lock the tensioning suture. In certain embodiments of the bone fixation system, the inner screw may assist a tensioning suture to be placed within the screw in a low-profile manner. The head or distal tensioning suture end may also or instead be held in place at/near the screw head via a knot, button, or any other mechanism/structure. The bone fixation system tensioning suture could be retained distal to the tip end of the screw via a button, tab, knot or other anchor structure which is operative to brace the tensioning suture against one of the patient tissue structures being placed under compression.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

It is to be appreciated that anatomical fractures, fissures, and displacements materialize in a variety of arrangements and severity. The various arrangements of fractures, fissures, and displacements described herein are by way of example. It will be apparent to those of skill in the art that the present invention is not limited to fractures, fissures and displacements of these types, and can also be effective in other types of injuries and repairs.

FIGS. 1-4 illustrate one non-limiting example of aspects of a bone fixation system 10 according to one aspect of the present disclosure. The bone fixation system 10 may include a screw 20, a length of suture 50, an anchor 60, and tensioning tab 80.

Figure 1:
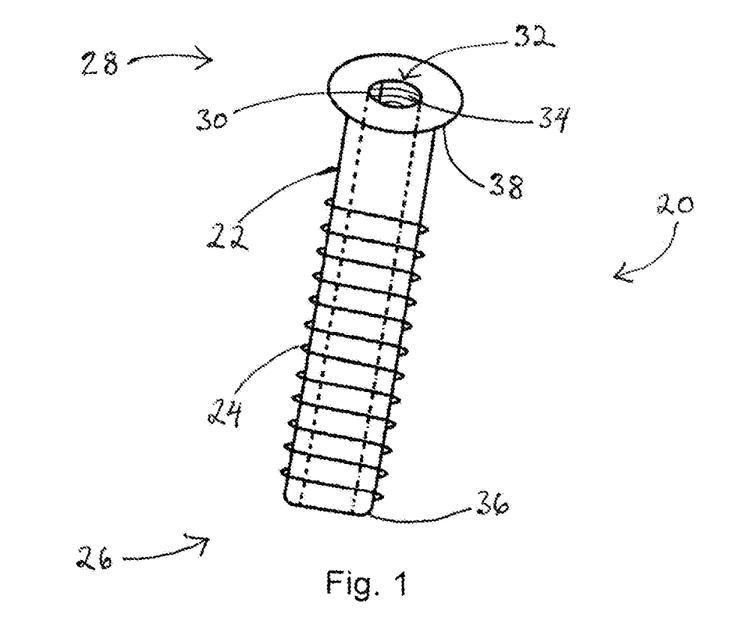
FIG. 1 is a front view of a cannulated screw having internal threads according to aspects of the present disclosure.
Figure 2:
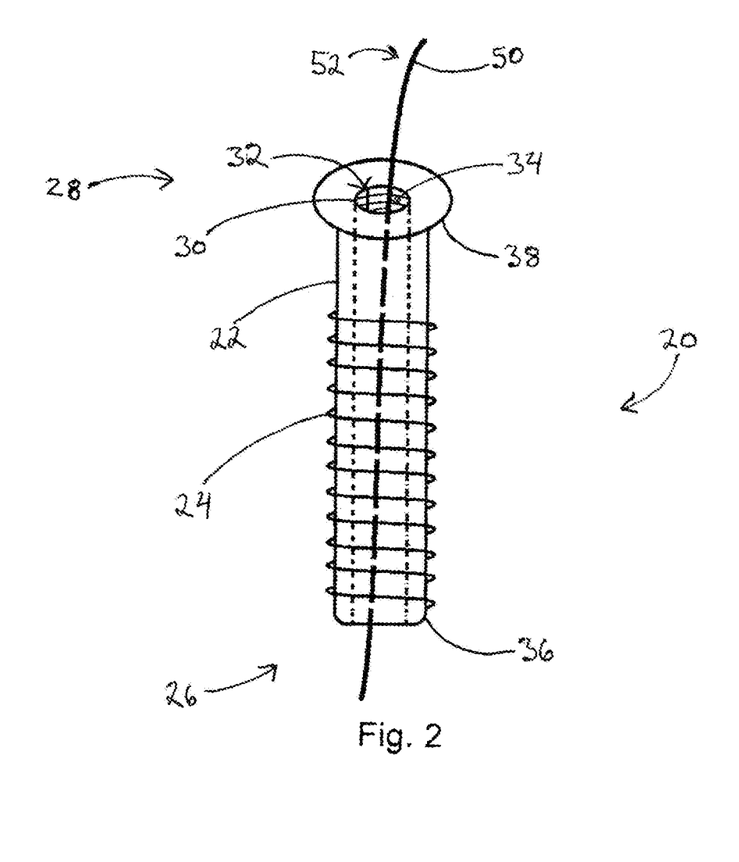
FIG. 2 is a front view of the cannulated screw of FIG. 1 having a suture extending through the cannula according to aspects of the present disclosure.

FIG. 1 illustrates the screw 20 of the bone fixation system 10. The screw 20 may include an elongated shaft 22, a threaded surface 24, a distal end 26, a proximal end 28, and internal surface 30 extending from the proximal end 28 to the distal end 26. The internal surface 30 may define a passageway 32 configured to receive the length of suture 50 (see FIG. 2). In one non-limiting example, the internal surface 30 may further include a threaded portion 34 at the proximal end 28 of the screw 20. The screw 20 may further include a smooth tip 36 located at the distal end 26 of the screw. A screw head 38 may be located at the proximal end of the screw 20 and extend radially outward from the elongated shaft 22. The screw 20 may be formed from titanium, a titanium alloy (e.g., Ti-6Al-7Nb, Ti-6Al-4V), stainless steel (e.g., 316L), or any biocompatible screw material. The suture 50 may be formed from ultra-high molecular weight polyethylene, or any biocompatible suture material.

Figure 3:
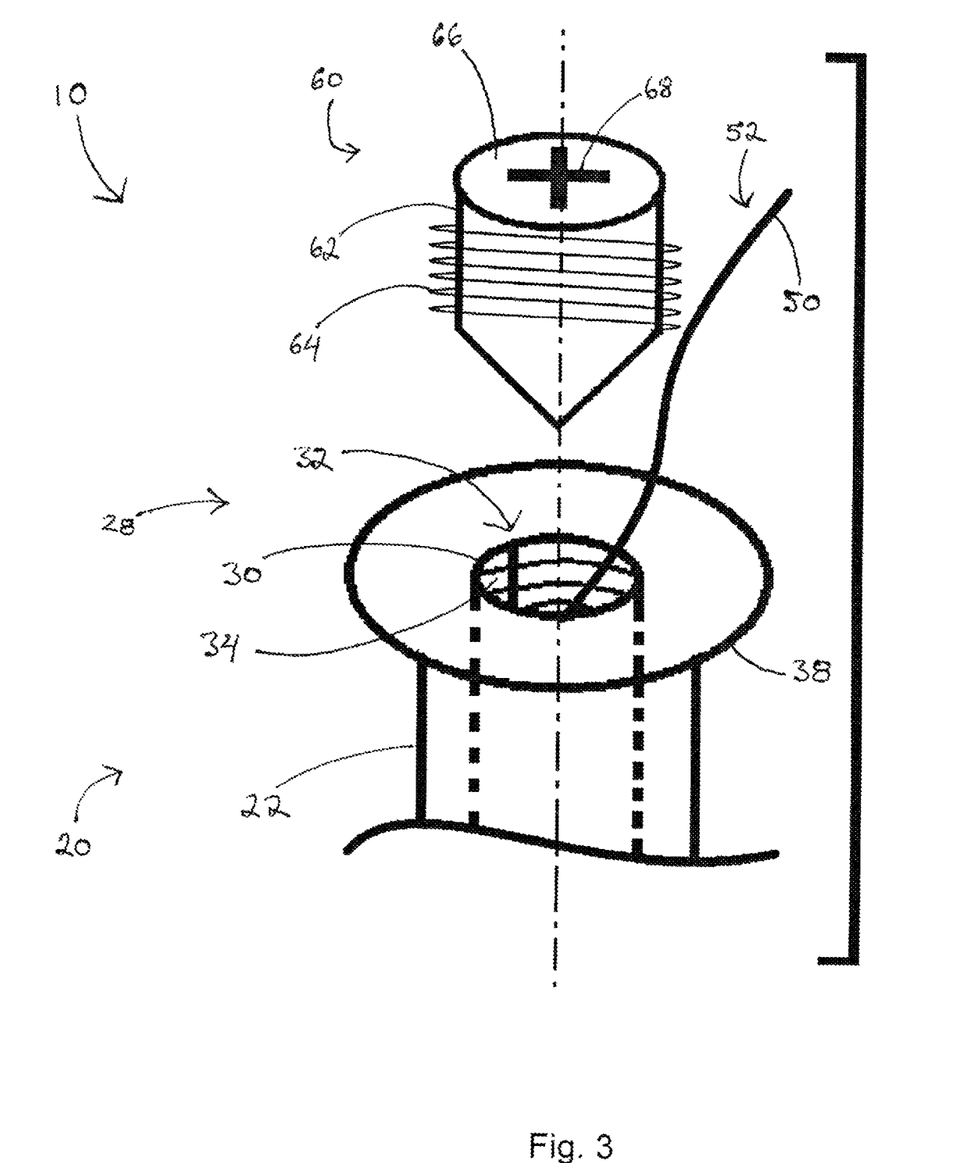
FIG. 3. is a detailed exploded view of the cannulated screw of FIG. 1 including an anchor according to aspects of the present disclosure.

As shown in FIG. 3, the bone fixation system 10 may further include an anchor 60. The anchor 60 may include a body 62 with external threads 64 configured to engage the threaded portion 34 of the internal surface 30 of the screw 20. The anchor 60 may further include a head 66 including a drive 68 dimensioned to receive a screwdriver or other driving device known in the art. In one non-limiting example, the drive 68 may be a Phillips driver. The anchor 60 may be formed from titanium, a titanium alloy (e.g., Ti-6Al-7Nb, Ti-6Al-4V), stainless steel (e.g., 316L), or any biocompatible material.

Figure 4:
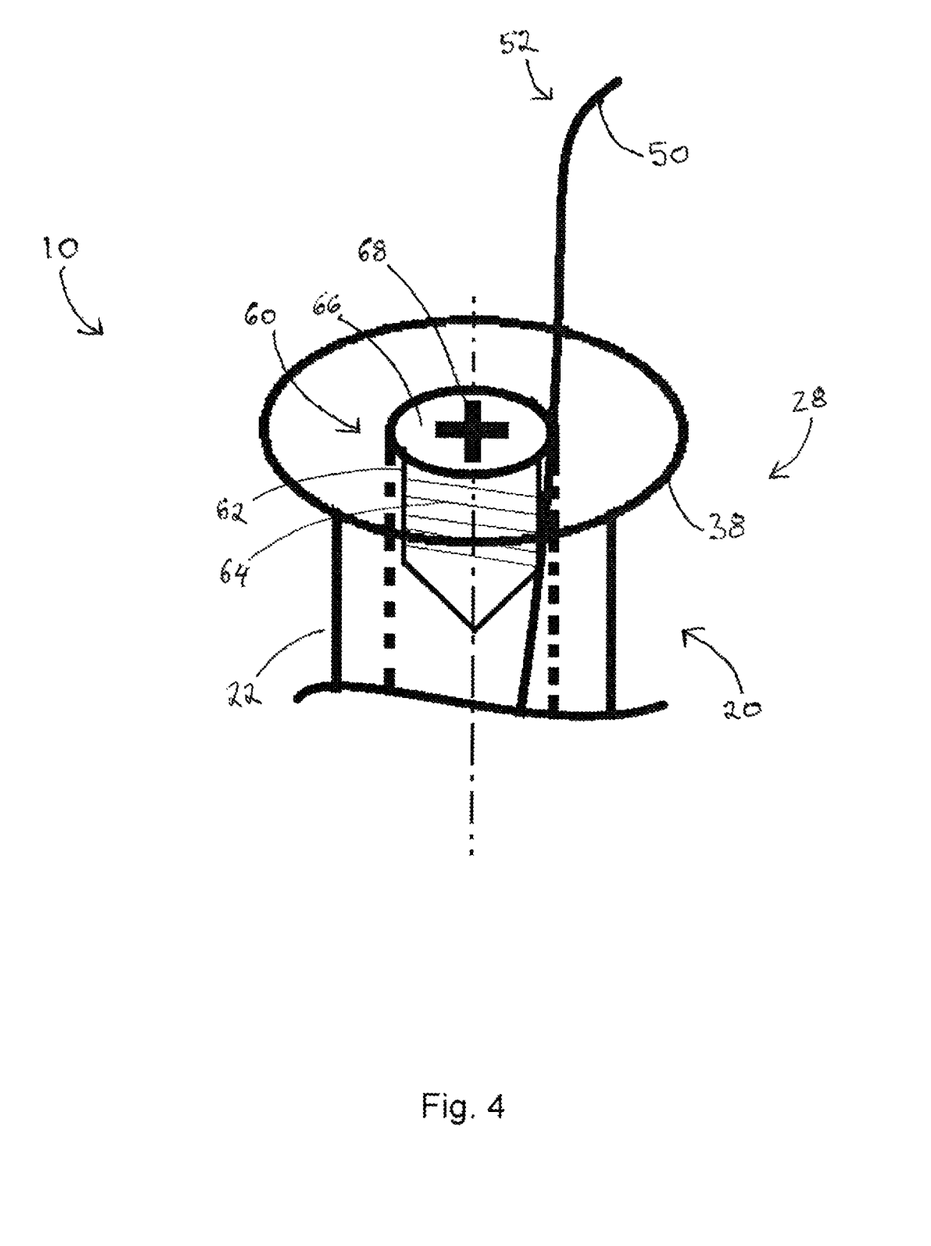
FIG. 4 is a detailed assembly view of the cannulated screw and the anchor of FIG. 3 according to aspects of the present disclosure.

FIG. 4 illustrates the anchor 60 received by the threaded portion 34 of the internal surface 30 of the screw 20. In one non-limiting example, the anchor 60 may secure the length of suture 50 at a first end 52. The first end 52 of the length of suture 50 may be secured as the anchor 60 is screwed into the threaded portion 34 of the internal surface 30 of the screw 20 via the drive 68. In one non-limiting example, the anchor 60 may secure the first end 52 of the length of suture 50 and a second end 54 of the length of suture 50.

Figure 5:
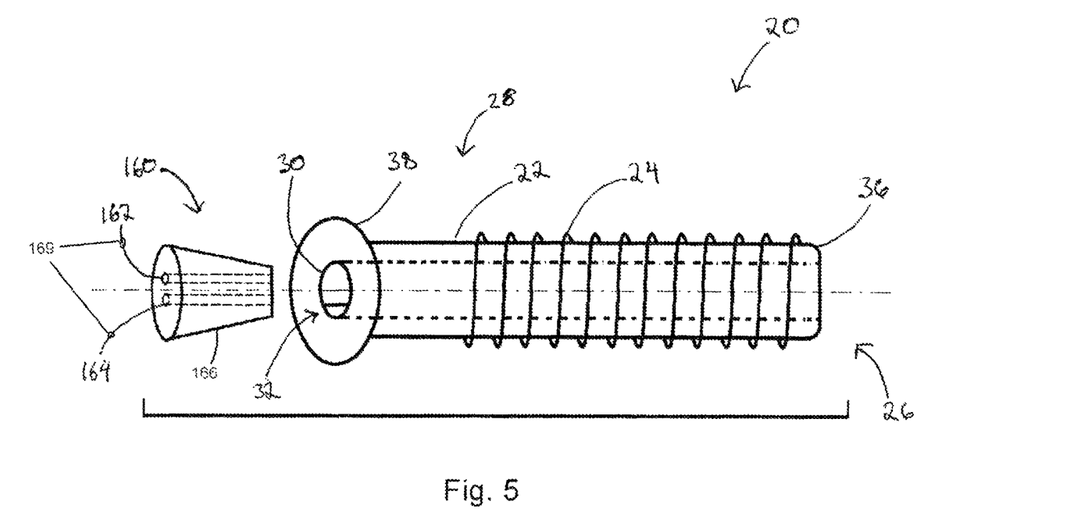
FIG. 5 is an exploded front view of a cannulated screw and anchor including two through holes according to aspects of the present disclosure.

FIG. 5 illustrates aspects of the bone fixation system 10 including an anchor 160 according to another aspect of the present disclosure. The anchor 160 may include a first through-hole 162, a second through-hole 164, and an external surface 166. The first through-hole 162 may be dimensioned to receive the first end 52 of the length of suture 50 and the second through-hole 164 may be dimensioned to receive the second end 54 of the length of suture 50.

Figure 6:
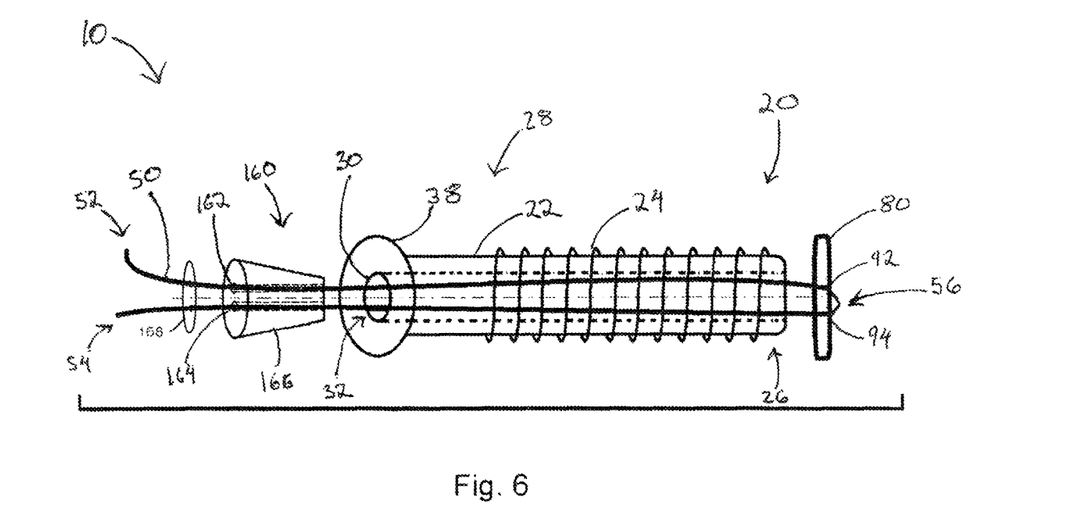
FIG. 6 is an exploded front view of the cannulated screw and anchor of FIG. 5, further including a suture and a tensioning tab according to aspects of the present disclosure.

As illustrated in FIG. 6, the external surface 166 of the anchor 160 may be dimensioned to create an interference fit with the internal surface 30 of the passageway 32 of the screw 20. The first end 52 and the second end 54 of the length of suture 50 may be secured at the proximal end 28 of the screw 20 by means of the anchor 160. The first end 52 and the second end 54 of the length of the suture 50 may engage the anchor 160, for example, via a knot (not shown). The first end 52 and the second end 54 of the length of suture 50 may alternatively be secured at the anchor 160 via a series of knots 169 as shown in FIG. 5, a button 168 as shown in FIG. 6, an adhesive, or any other suture securement method known in the art. The button 168 has a disk shape; however, other shapes such as a cylinder or a polygonal prism (e.g., rectangular prism) are suitable.

Further illustrated in FIG. 6, a midsection of suture 56 may be affixed to a tensioning tab 80 adjacent to the distal end 26 of the screw 20. The tensioning tab 80 may include a first aperture 92 and a second aperture 94 dimensioned to receive the length of suture 50. The tensioning tab 80 has a disk shape; however, other shapes such as a cylinder or a polygonal prism (e.g., rectangular prism) are suitable. The tensioning tab 80 may be formed from titanium, a titanium alloy (e.g., Ti-6Al-7Nb, Ti-6Al-4V), stainless steel (e.g., 316L), or any biocompatible material.

As illustrated below in example embodiments, the screw 20 of the bone fixation system 10 may first enter a first side of a bone tunnel and extend substantially through at least a first bone, for example, such that the elongated shaft 22 intersects a fracture or a second bone. The bone tunnel extends from the first side to the second side between a first bone surface and a second bone surface. The tensioning tab 80 is configured to engage the second bone surface and provide tension to the length of suture 50 when the first end 52 and the second end 54 of the length suture are secured via a method described above at the proximal end 28 of the screw 20. In another non-limiting example, the tensioning tab 80 may be affixed to the second end 54 of the length of suture 50 and provide tension to the length of suture 50 when the tensioning tab is engaged with the second bone surface and the first end 52 of the length of suture 50 is secured via a method described above at the proximal end 28 of the screw 20. The tensioning tab 80 may be dimensioned to pass through the bone tunnel.

Figure 7:
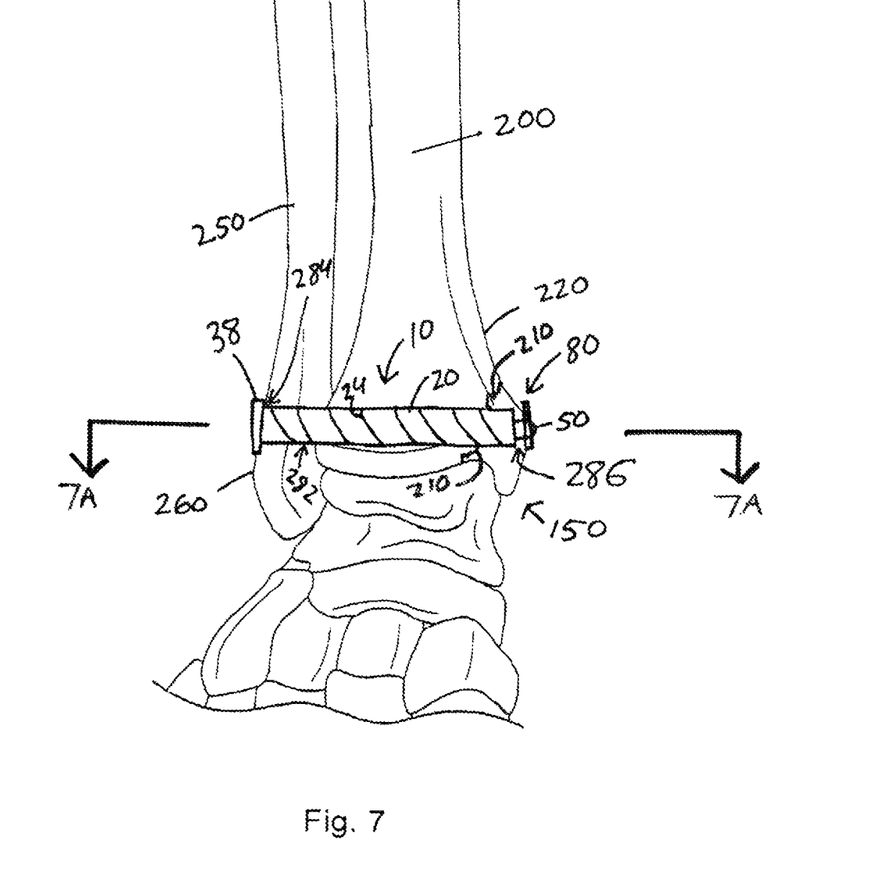
FIG. 7 is a front view of a bone fixation system according to the invention being used in an ankle syndesmosis repair system.

Turning now to FIG. 7, a bone fixation system 10 according to the present disclosure may be used for stabilizing the syndesmosis of an ankle 150. The screw 20 of the bone fixation system 10 is installed into the ankle 150 such that the threaded surface 24 passes through the fibula 250 and into the tibia 200. The screw 20 of the bone fixation system 10 may first enter a first side 284 of a bone tunnel 282 and extend substantially through at least a first bone such that the elongated shaft 22 intersects a fracture. The bone tunnel 282 extends from the first side 284 to the second side 286 between a lateral surface 260 of the fibula 250 and a medial surface 220 of the tibia 200. The bone tunnel 282 may be prepared by drilling through the cortical bone and cancellous bone of the fibula 250 and the tibia 200. The head 38 of the screw 20 of the bone fixation system 10 engages the lateral surface 260 of the fibula 250, and the tensioning tab 80 of the bone fixation system 10 is positioned to engage the medial surface 220 of the tibia 200 having a fracture 210. When the length of suture 50 is tensioned as described above, a compressive force is generated across the tibia fracture 210 thereby helping fracture healing.

Figure 7A:
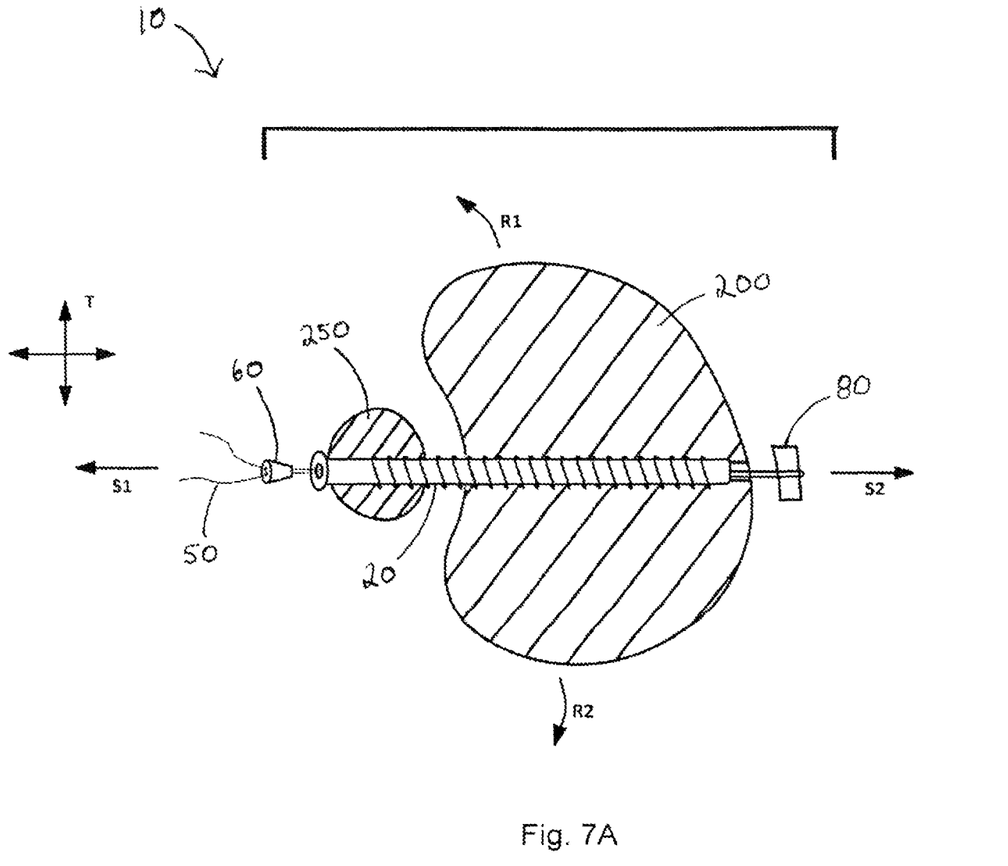
FIG. 7A is an exploded cross-sectional view of the ankle syndesmosis repair system of FIG. 7 taken along lines 7A-7A of FIG. 7.

Looking at FIG. 7A, some advantages of using the bone fixation system 10 in the ankle syndesmosis repair system of FIG. 7 are shown. Specifically, when the bone fixation system 10 is implanted in the tibia 200 and the fibula 250 of the ankle 150, the screw 20 of the bone fixation system 10 resists translation of the tibia 200 and the fibula 250 in directions T shown in FIG. 7A. In addition, the screw 20 of the bone fixation system 10 resists rotation of the tibia 200 and the fibula 250 in directions R1 and R2 shown in FIG. 7A. When the bone fixation system 10 is implanted in the ankle 150, the tensioning components, i.e., the suture 50, the anchor 60, and the tensioning tab 80, resist in-line distraction/separation in directions S1 and S2 shown in FIG. 7A.

Figure 8:
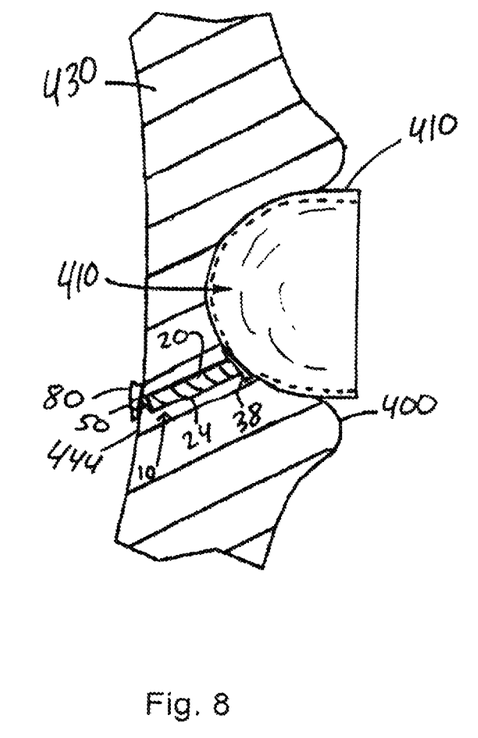
FIG. 8 is a cross-sectional view of an acetabular shell of a hip prosthesis secured in the acetabular cavity of a hip using a bone fixation system according to the invention.

Referring now to FIG. 8, a bone fixation system 10 according to the present disclosure may be used for implanting an acetabular shell 410 of a hip prosthesis in a hip bone. First, the acetabulum 400 of the hip bone 430 is inspected and tools such as a reamer may be used to clean material out of the acetabular cavity. Once the acetabular cavity has been prepared, a surgeon can use an access channel present in the acetabular shell 410 as a location for the screw 20 of bone fixation system 10 according to the present disclosure. The screw 20 penetrates through the hip bone 430, and the head 38 of the screw 20 of the bone fixation system 10 engages the acetabular shell 410, and the tensioning tab 80 of the bone fixation system 10 is positioned to engage a medial surface 444 of the hip bone 430. When the length of suture 50 is tensioned as described above, a compressive force is generated thereby securing the acetabular shell 410 to the hip bone 430.

Figure 9:
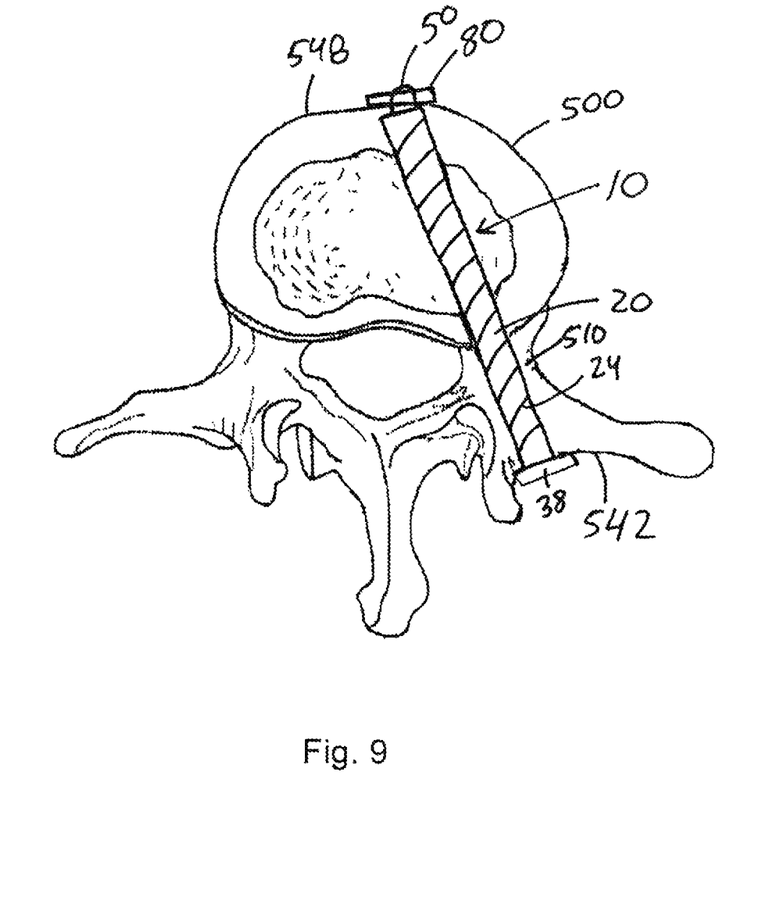
FIG. 9 is a top view of a bone fixation system according to the invention installed onto a vertebra.

Turning now to FIG. 9, a bone fixation system 10 according to the present disclosure may be used for pedicle screw fixation. The screw 20 of the bone fixation system 10 is installed into the vertebra 500 such that the threaded surface 24 passes through the pedicle 510 of the vertebra 500. The head 38 of the screw 20 of the bone fixation system 10 engages a posterior surface 542 of the vertebra 500, and the tensioning tab 80 of the bone fixation system 10 is positioned to engage an anterior surface 548 of the vertebra 500. When the length of suture 50 is tensioned as described above, a compressive force is generated thereby securing the screw 20 to the vertebra 500. The compressive force increases the structural stability of the screw 20 and aids in preventing the screw 20 from backing out of the vertebra 500.

Figure 10:
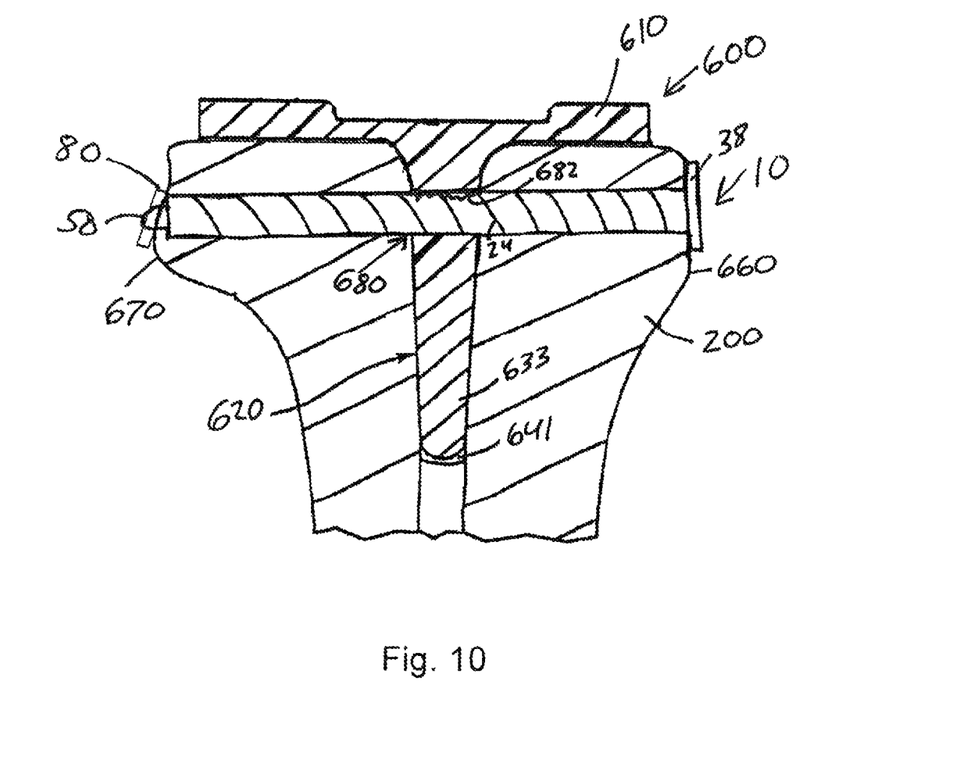
FIG. 10 is a cross-sectional view of a tibial implant of a knee prosthesis secured in the proximal end of a tibia using a bone fixation system according to the invention.

Referring now to FIG. 10, a bone fixation system 10 according to the present disclosure may be used for implanting a tibial implant 600 of a knee prosthesis in a tibia 200. The tibial implant 600 has a body portion 610 and a stem 620 which extends outward from the body portion 610. The body portion 610 is affixed to the end surface of the proximal end of the tibia 200. A bearing element (not shown) is affixed to the tibial implant 600, and the bearing element articulates with a femoral knee prosthesis (not shown) as is well known in the art. The distal portion 633 of the stem 620 of the tibial implant 600 extends into the medullary canal 641 of the tibia 200. The screw 20 of the bone fixation system 10 is installed into the tibia 200 such that the threaded surface 24 passes through the tibia 200. The head 38 of the screw 20 of the bone fixation system 10 engages a lateral surface 660 of the tibia 200, and the tensioning tab 80 of the bone fixation system 10 is positioned to engage a medial surface 670 of the tibia 200. The screw 20 is inserted through an access channel 680 of the stem 620 of the tibial implant 600. The access channel 680 may have internal threads 682 to engage the threaded surface 24 of the screw 20. The length of suture 50 may be tensioned as described above to keep the tibial implant 600 secured in the tibia 200.

Figure 11:
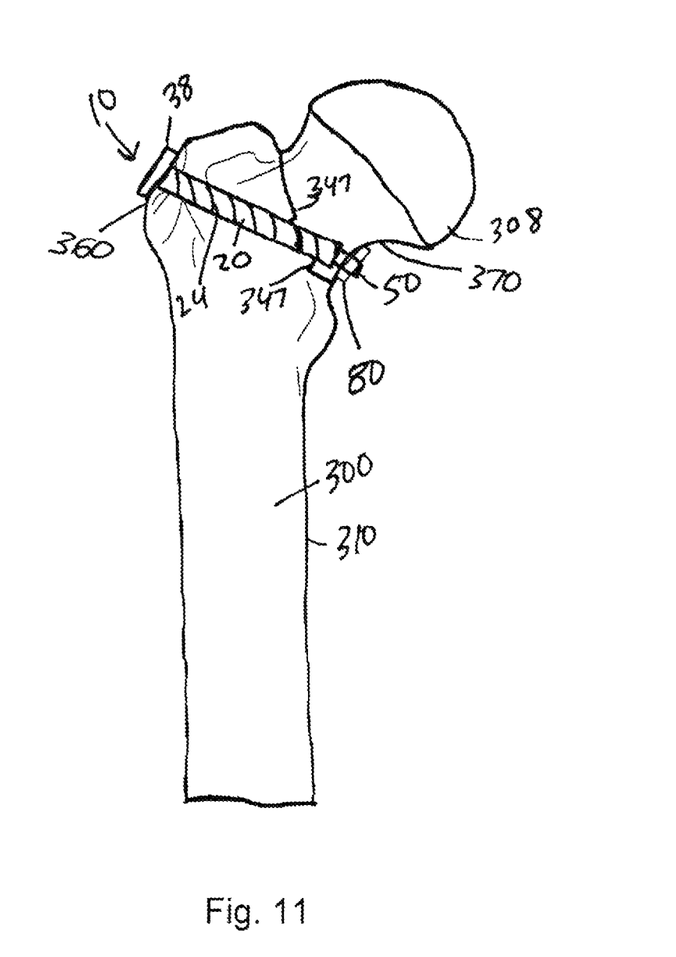
FIG. 11 is a side view of a bone fixation system according to the invention being used in fixation of a femur bone having a fracture.

Turning now to FIG. 11, a bone fixation system 10 according to the present disclosure may be used for fixation of a femoral head fracture. The screw 20 of the bone fixation system 10 is installed into the femur 300 such that the threaded surface 24 passes through the femur 300. The head 38 of the screw 20 of the bone fixation system 10 engages a lateral surface 360 of a femur 300 having a femoral head 308 and a femoral shaft 310, and the tensioning tab 80 of the bone fixation system 10 is positioned to engage a medial surface 370 of a femur 300 having a fracture 347. When the length of suture 50 is tensioned as described above, a compressive force is generated across the femoral fracture 347 thereby helping fracture healing.

Thus, the invention provides an improved bone fixation system. More particularly, the invention provides a bone fixation system that achieves a low profile solution that utilizes the rotational control of a screw with the pullout strength of suture buttons/tension cords, using a cannulated screw that interfaces directly with a tensioning suture system.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A bone fixation system comprising:
   a length of suture having a first end and a second end;
   a screw comprising an elongated shaft having a threaded external surface, wherein the screw has a distal end, a proximal end, and an internal surface defining a passageway within the screw extending between the distal end and the proximal end, the passageway being configured to receive the length of suture;
   a tensioning tab affixed to a section of the length of suture; and
   an anchor configured to secure the first end of the length of suture adjacent to the proximal end of the screw.

2. The bone fixation system of claim 1, wherein the section is a midsection between the first end and the second end.

3. The bone fixation system of claim 1, wherein the anchor is configured to secure the second end of the length of suture adjacent to the proximal end of the screw.

4. The bone fixation system of claim 1, wherein the anchor is dimensioned to create an interference fit inside the passageway.

5. The bone fixation system of claim 1, wherein the internal surface includes a threaded portion at the proximal end of the screw configured to engage the anchor.

6. The bone fixation system of claim 5, wherein the anchor includes external threads configured to engage the threaded portion of the internal surface.

7. The bone fixation system of claim 1, wherein the anchor includes at least one through hole configured to receive the length of suture.

8. The bone fixation system of claim 1, wherein the length of suture comprises a knot configured to engage the anchor.

9. The bone fixation system of claim 1, further comprising a button configured to engage the anchor and the length of suture.

10. The bone fixation system of claim 1, wherein the distal end terminates in a smooth tip.

11. The bone fixation system of claim 1, wherein the tensioning tab is dimensioned to navigate from a first side of a bone tunnel to a second side of the bone tunnel, wherein the bone tunnel extends from a first bone surface to a second bone surface, the tensioning tab being configured to engage the second bone surface.

12. The bone fixation system of claim 1, wherein the tensioning tab includes a first aperture.

13. The bone fixation system of claim 12, wherein the tensioning tab includes a second aperture.

14. The bone fixation system of claim 11, wherein the elongated shaft extends through the bone tunnel from the first bone surface to substantially adjacent to the second bone surface.

15. The bone fixation system of claim 14, wherein the bone tunnel extends through a bone selected from a tibia, a fibula, a femur, an acetabulum, or a vertebra.

16. The bone fixation system of claim 14, wherein the bone tunnel extends through a tibia and a fibula.

* * * * *